(12) United States Patent
Sandrin et al.

(10) Patent No.: US 8,419,642 B2
(45) Date of Patent: Apr. 16, 2013

(54) DEVICE FOR MEASURING THE VISCOELASTIC PROPERTIES OF BIOLOGICAL TISSUES AND METHOD USING SAID DEVICE

(75) Inventors: Laurent Sandrin, l'Hay-les-Roses (FR); Sylvain Yon, Fontenay aux roses (FR)

(73) Assignee: Echosens, Paris (FR)

( * ) Notice: Subject to any disclaimer, the term of this patent is extended or adjusted under 35 U.S.C. 154(b) by 550 days.

(21) Appl. No.: 12/532,040

(22) PCT Filed: Mar. 20, 2008

(86) PCT No.: PCT/FR2008/000374
§ 371 (c)(1),
(2), (4) Date: Nov. 5, 2009

(87) PCT Pub. No.: WO2008/135659
PCT Pub. Date: Nov. 13, 2008

(65) Prior Publication Data
US 2010/0130865 A1    May 27, 2010

(30) Foreign Application Priority Data

Mar. 21, 2007 (FR) ..................... 07 02050

(51) Int. Cl.
*A61B 8/00* (2006.01)
(52) U.S. Cl.
USPC .......................................... 600/438
(58) Field of Classification Search ............ 600/438
See application file for complete search history.

(56) References Cited

U.S. PATENT DOCUMENTS

| 2004/0167403 A1 | 8/2004 | Nightingale et al. |
| 2006/0207343 A1* | 9/2006 | Clifton et al. .................. 73/841 |

FOREIGN PATENT DOCUMENTS

| EP | 1 623 675 | 2/2006 |
| EP | 1 040 789 | 3/2007 |
| FR | 2 844 058 | 3/2004 |
| FR | 2869 521 | 11/2005 |

OTHER PUBLICATIONS

International Search Report for Appln. No. PCT/FR2008/000374.

* cited by examiner

*Primary Examiner* — Unsu Jung
*Assistant Examiner* — Saurel J Selkin
(74) *Attorney, Agent, or Firm* — Pillsbury Winthrop Shaw Pittman, LLP

(57) ABSTRACT

A device configured to measure the viscoelastic properties of biological tissues using a processing of ultrasound waves reflected by these tissues when a shear wave runs across them is presented. The device includes memories for forming lines of data such that each line comprises data relative to the ultrasound waves reflected from the same shot and a calculator for determining a parameter relative to the displacement between the tissues and a transducer emitting the shots, a calculator for calculating an intrinsic displacement of the medium from a set of lines forming an acquisition, and a processor for processing the first ultrasound lines, by using the relative parameter, before or during the formation of second ultrasound lines from this same acquisition, in order to determine the intrinsic displacement of the biological tissues from these first lines.

16 Claims, 5 Drawing Sheets

DEVICE FOR MEASURING THE VISCOELASTIC PROPERTIES OF BIOLOGICAL TISSUES AND METHOD USING SAID DEVICE

CROSS-REFERENCE TO RELATED APPLICATIONS

This is the U.S. National Stage of PCT/FR2008/000374, filed Mar. 20, 2008, which in turn claims priority to French Patent Application No. 0702050, filed Mar. 21, 2007, the entire contents of both applications are incorporated herein by reference in their entireties.

The invention relates to a device for measuring the viscoelastic properties of biological tissues and to a method using this device.

Elastography performs a non-invasive measurement of the viscoelastic properties, subsequently referred to as VP, of biological tissues in order to enable the diagnosis, screening or follow-up of treatments relating to, for example, organs such as the liver, skin or blood vessels.

Such a method is described, for example, in patent application FR 2869521, filed on 3 May 2004 in the name of the Echosens Corporation, whose content is incorporated in this application for reference.

With reference to FIG. 1, the operation of a device 10 implementing this method may be carried out in three steps:

A first step during which the device 10 acquires and stores ultrasound data in a memory.

To do this, ultrasound waves are emitted into tissues observed by means of one or more transducers.

The emission of each ultrasound wave, subsequently referred to as a shot, generates reflected ultrasound waves as the ultrasound wave emitted is propagated in the biological tissues comprising diffusing particles.

Data relative to the reflected ultrasound waves may be collected by the device 10, the data from ultrasound waves reflected during a shot i forming an ultrasound line Li stored in a dedicated memory Mi.

The set of n ultrasound lines $L_1, L_2, L_3, L_4, L_5 \ldots L_n$ specific to a VP measurement comprising a sequence of shots T1, T2, T3, T4, T5, ... Tn is referred to as an acquisition 1A stored by using memories M1, M2, M3, M4, M5, ... Mn.

A second step 2 during which the acquisition 1A is transferred to a first calculator 5. Such a transfer allows the acquisition 1A to be processed by using components dedicated to the calculations described subsequently.

A third step 3 of transferring the results from the processing calculations to lead to the VP E values of the biological tissues observed.

To obtain these E values, the device 10 must perform a series 4 of intermediate calculations aiming to obtain a table 1D of displacements of tissues observed according to their distance in relation to a transducer performing the emission—the transducer being run by a low frequency movement less than 500 Hz—and/or the reception of ultrasound waves. This distance is also subsequently referred to as "depth."

To do this, the first calculator 5 determines a table 1B of parameters of relative displacements from the transducer with relation to the observed tissues.

Then a calculator 6 uses this table 1B of relative displacement parameters to correct the acquisition 1A and to obtain a corrected acquisition 1C compensating for the relative displacements of the transducer.

Lastly, a calculator 7 determines, on the basis of the corrected acquisition 1C, the table 1D of tissue displacements specific to the observed tissues. This displacement of tissues is subsequently referred to as the intrinsic displacement.

This operation may be performed by a technique known as autocorrelation, intercorrelation or, more generally, by any technique for measuring displacements from ultrasound signals.

ii) From this table 1D of intrinsic displacements, an E measurement of the VP of observed tissues may be determined by a calculator 8.

The invention results from the observation that such a device 10 presents disadvantages. In particular, this device requires numerous memories Mi, of relatively large size, to store an acquisition 1A, a table 1B of relative displacement parameters, a corrected acquisition 1C and/or a table 1D of intrinsic displacements.

Such being the case, the cost and size of these memories are high, particularly due to the fact that they require means for high-speed data processing—several megabytes/sec. Thus, the cost and bulkiness, of a device 10 equipped with these memories increases proportionally.

In addition, numerous data transfers must be managed to/in the device 10. Because of this, the device 10 comprises numerous data transfer means that further increase its cost and bulkiness.

In addition, these calculations and transfers require a significant time between the emission of a sequence of ultrasound shots and the receipt of an associated VP measurement.

For example, the storage of an acquisition 1A typically requires a duration on the order of 100 ms for a maximum depth on the order of 100 mm in one-dimensional pulsed elastography.

In addition, the duration necessary for transferring data and performing various calculations required within the device 10 reaches several seconds by considering a single depth axis.

Lastly, the data to transfer are grouped together and typically present volumes of several megabytes. A rapid transfer of these data groups requires the use of a high-speed connection with a high cost, while the use of low-speed connections increases transfer times by several seconds. Typically, the transfer 2 of an acquisition 1A whose size is 4 megabytes necessitates 3.4 seconds with a 10 mbps connection.

The invention aims to resolve at least one of the previously indicated problems. This is why the invention relates to a device intended to measure the VP of biological tissues using a processing in which ultrasound waves are reflected by the tissues when a shear wave runs across them, this device comprising means for:

forming an acquisition with the ultrasound lines such that each ultrasound line comprises data relative to the ultrasound waves generated by reflection of the same shot, and determining a parameter relative to the displacement of an ultrasound transducer with relation to the tissues, this device being characterized in that the device comprises means to process the first ultrasound lines of the acquisition, by using the relative parameter, before the acquisition of second ultrasound lines from this same acquisition in order to determine the intrinsic displacement of biological tissues from these first lines.

Thanks to such a device, it is possible to process ultrasound lines during an acquisition, that is to say, as and when the lines from the same acquisition are formed.

Thus, the acquisition processing time is greatly reduced since a device in conformance with the invention may start processing lines of an acquisition as soon as the first lines of this acquisition are formed.

As a reminder, the processing of an acquisition starts, according to the prior art, when the last line of this acquisition is formed.

Thanks to the invention, numerous lines of an acquisition have been processed before the last line of this acquisition is formed. Thus, the time necessary for obtaining a measurement of the intrinsic displacement of the observed tissues is considerably reduced.

Generally, by considering Δ(cal) the processing time of two lines and n the number of lines of an acquisition, the prior art performs an acquisition ending at the earliest after a time greater than (n−1)*Δ(cal) as from the end of the acquisition, the data transfer times being deemed zero.

Under similar conditions, a device in conformance with the invention may complete the processing of an acquisition after a time on the order of Δ(cal) counting from the end of the acquisition.

A device in conformance with the invention also presents the advantage of considerably reducing the number of memories and data transfers necessary for processing lines.

In fact, a limited size memory may be implemented to store a reduced number of lines since only the lines being processed and/or acquired must be stored.

In fact, the storage of lines already processed is not necessary and the memory allocated to such already-processed lines may be released and allocated to other lines.

In one embodiment, the device comprises, means for calculating the displacement intrinsic to a given time and depth.

According to one embodiment, the device comprises means for determining various intrinsic displacements so as to form at least one chronological table with these intrinsic displacements, each column of the table being function of the depth at which the intrinsic displacements are measured.

In one embodiment, the device comprises means so that the calculation time of an intrinsic displacement is less than the time separating two successive ultrasound shots.

According to one embodiment, the device comprises means so that the memory allocated to a first ultrasound line is made available, after processing, to store a subsequent ultrasound line.

In one embodiment, the device comprises means so that only two lines corresponding to an intrinsic displacement calculation in progress, as well as line (Ln+2) being acquired, are stored by the device.

According to an embodiment, the same calculator simultaneously performs operations connected to an ultrasound line formation and to an intrinsic displacement calculation.

In one embodiment, the device comprises means so that the processed ultrasound lines come from a single emitter/receiver element.

According to one embodiment, the device comprises means so that the ultrasound lines are formed thanks to electronic focusing with at least one transducer comprising several elements.

In one embodiment, the device comprises means to calculate a relative displacement of the transducer with relation to the observed tissues by using, at least:
- one external physical measurement, such as the position of said transducer with relation to a given referential,
- shaping of a biophysical measurement, such as a signal obtained from a heart or rate, or
- a calculation performed from ultrasound data.

In one embodiment, the device comprises means so that the intrinsic displacement represents or derives from at least one of the following elements: a measurement of displacement, speed, deformation speed and a deformation measurement.

According to one embodiment, the device comprises means to process concurrently different acquisitions performed on different geometrical axes.

In one embodiment, the device comprises means to carry out measurements continuously.

The present invention also relates to a method implementing a device in conformance with one of the previous embodiments.

The invention also relates to a probe dedicated to measuring the VP of biological tissues by elastography, characterized in that the probe comprises a device in conformance with one of the previous, embodiments.

Other characteristics and advantages of the invention will appear in light of the description of an embodiment of the invention carried out below, for illustrative and non-limiting purposes, by referring to the attached figures in which:

FIG. 1, already described, is a flow sheet of a known VP measuring device, and

A device in conformance with the invention measures the VP of biological tissues by elastography, that is, using the processing of ultrasound waves reflected by these tissues when a shear wave runs across them.

Figure 2:
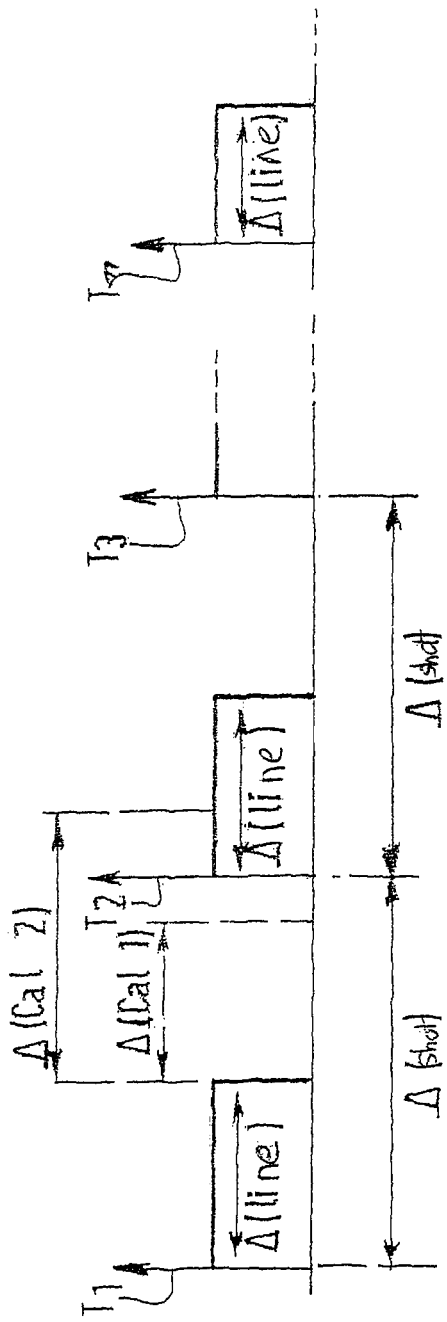
FIG. 2 represents different times implemented during an acquisition.

With reference to FIG. 2, such a device uses shots T1, T2, T3, . . . Tn of ultrasound waves whose frequency is typically between 1 and 10 MHz, and more generally between 0.1 and 40 MHz.

These shots are performed by respecting a time Δ(shot) between each shot of between 0.1 ms and 2 ms, more generally between 0.05 ms and 10 ms.

After each shot, data relative to the waves reflected by a shot T1, T2, T3, . . . Tn are used to form lines L1, L2, L3, . . . Ln of duration Δ(line) of between 50 and 100 μs, and more generally between 5 and 1000 μs.

It should also be noted that the VP measurement of a medium is performed from the measurement of a parameter relative to the propagation of elastic shear waves—such as the shear speed or viscosity—wherein the speed is typically between 1 and 10 m/s, more generally between 0.1 and 20 m/s.

By way of example, the VP measured may be the shear modulus, noted μ, obtained from the shear speed measurement noted Vs by using the following equation:

$$\mu = \rho V s^2$$

Where ρ is the density of the medium studied.

These shear waves are generated by any means, such as an electrodynamic transducer placed at the surface of tissues, an ultrasound transducer used to displace tissues remotely by radiation pressure or movements internal to the tissues linked to a biophysical activity, such as a heart or respiratory activity.

In a first variation of the invention, a device in conformance with the invention is considered, comprising calculation and transfer means such that the device may determine, from a partial acquisition comprising two successively formed, lines L1 and L2:

a parameter relative to the displacement of the transducer with relation to the observed tissues, a corrected partial acquisition, and an intrinsic displacement, During a calculation period Δ(call) of less than the time Δ(shot) between two successive shots reduced by the time Δ(line) necessary for forming a line.

In this situation, represented in dashes in FIG. 2, a device in conformance with the invention may process lines by using two memories M11 and M2 such that each memory is dedicated to the formation of a single line.

By repeating these operations, a device in conformance with the invention disposes intrinsic displacements of two first lines when the second lines are formed.

In fact, the content of memory L1 may be replaced by the data specific to a new line L3 subsequently formed with relation to processed lines L1 and L2. Thus, one may determine, for lines L2 and L3, similarly to lines L1 and L2:

a second parameter relative to the displacement, a second corrected partial acquisition, and a second intrinsic displacement.

As already indicated, such an operation saves considerable time and requires reduced data processing and transfer means since the lines are processed as and when they are formed. A second variation of the invention may be particularly implemented when, as represented in solid lines in FIG. 2, the calculation time Δ(cal2) is greater than the shot time Δ(shot) reduced by the line formation time Δ(line).

In this case, a device in conformance with the invention may operate with three memories M1, M2 and M3 by storing in a memory a line in formation while two other memories store two lines that are already formed and being processed.

Figure 3:
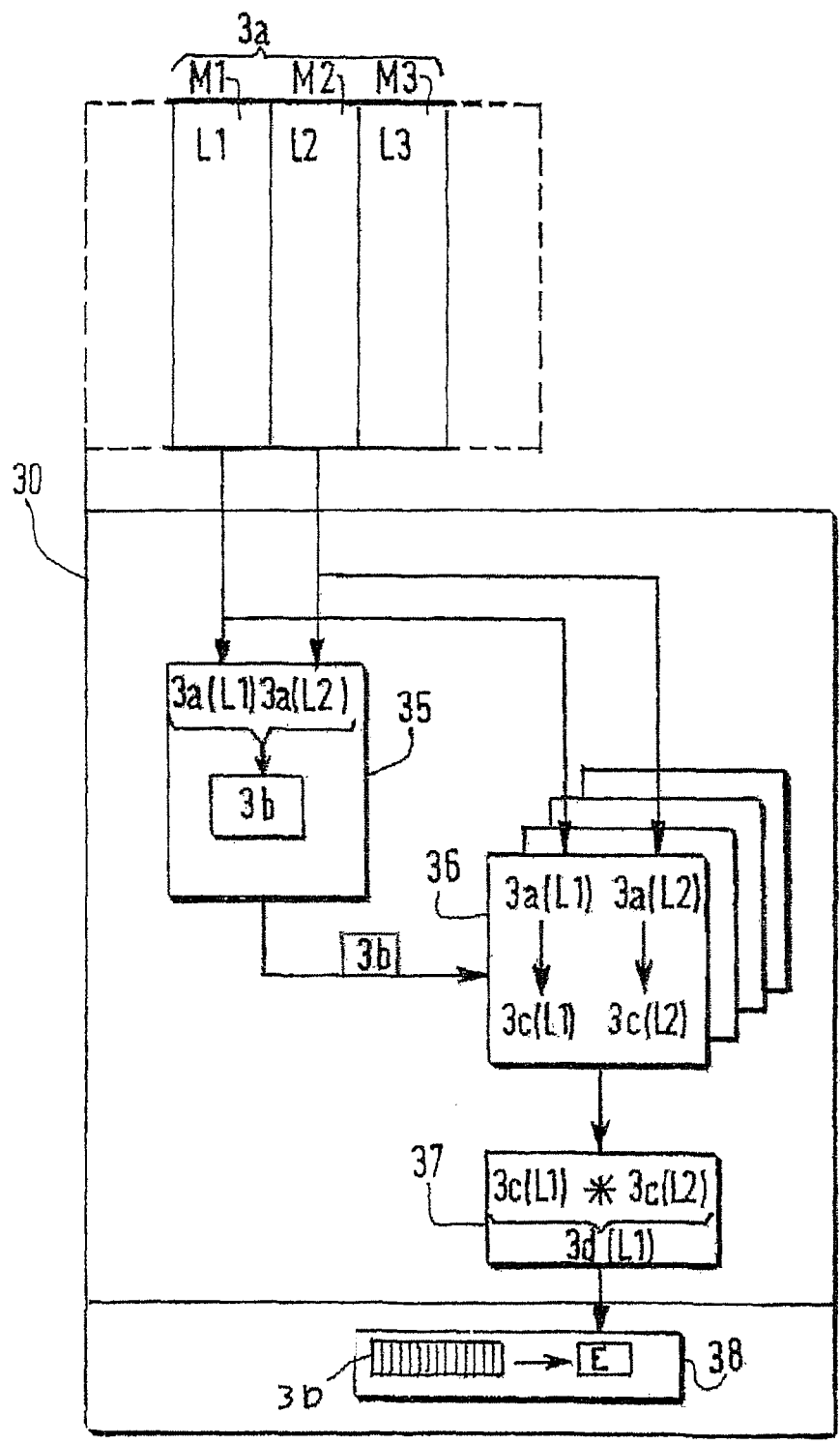
FIG. 3 is a flow sheet of a VP measuring device in conformance with the invention.

More precisely, such a device 30—FIG. 3—comprises means to use a partial acquisition 3a with lines $L_1$, $L_2$ and $L_3$ of ultrasound data.

It should be noted that this partial acquisition 3a uses a reduced size memory with relation to the memory required for the acquisition 1A according to the prior art.

Effectively and in conformance with the invention, first ultrasound lines. $L_1$ and $L_2$ are processed by means of a parameter 3b relative to the displacement, of the transducer in relation to the tissues, before the formation of second lines from this same acquisition.

To do this, the device 30 comprises a calculator 35 processing a partial acquisition 3a(L1) 3a(L2) limited to these first lines. $L_1$ and $L_2$ by determining the parameter 3b relative to the displacement between the relevant ultrasound transducer—generally the ultrasound wave emitter/receiver transducer—and the observed tissues.

In addition, device 30 comprises a calculator 36 determining a corrected partial acquisition 3c(L1) 3c(L2) allowing, by using a calculator 37, the intrinsic displacement 3d(L1) of biological tissues to be obtained at a time t and at a depth z.

Figure 1:
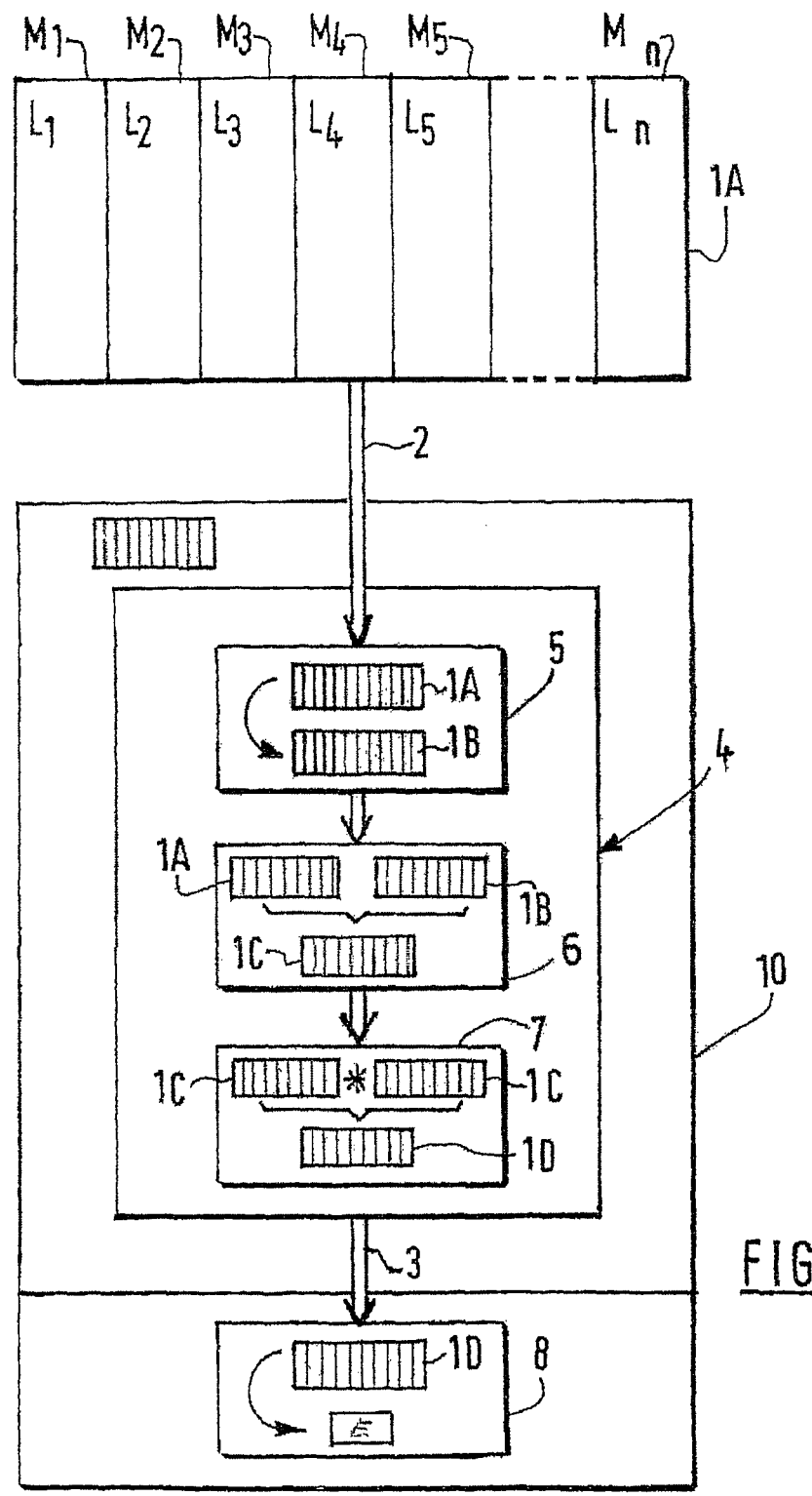

By using the successive processing of lines by a calculator 38, different intrinsic displacements 3d(L1) may be obtained so as to form progressively a table 3D similar to the table 1D formed according to the prior art, represented in FIG. 1.

More precisely, each column from table 3D contains intrinsic displacements measured for the same shot, and thus at a given time noted t, according to the depth noted z at which this intrinsic displacement 3D is measured.

However, the calculation time necessary for obtaining this table is greatly reduced since it is performed as and when the lines are formed and processed.

In addition, the memory used to store data relative to a first ultrasound line $L_1$ that is already processed may be made available.

In one embodiment, the same calculator 36 performs simultaneous operations linked to storage of ultrasound lines $L_1$ and $L_2$ and to calculating the intrinsic displacement from these lines.

For this purpose, this calculator concurrently receives data relative to these lines $L_1$ and $L_2$, the parameter 3b relative to the displacement then being determined for the latter by calculator 35.

Figure 4A:
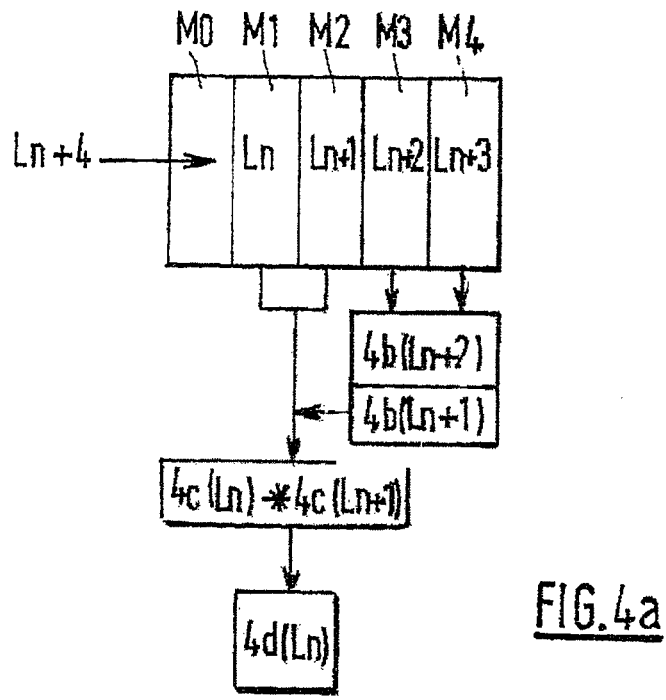
FIGS. 4a and 4b are flow sheets of a VP measuring device, in conformance with a second embodiment of the invention.
Figure 4B:
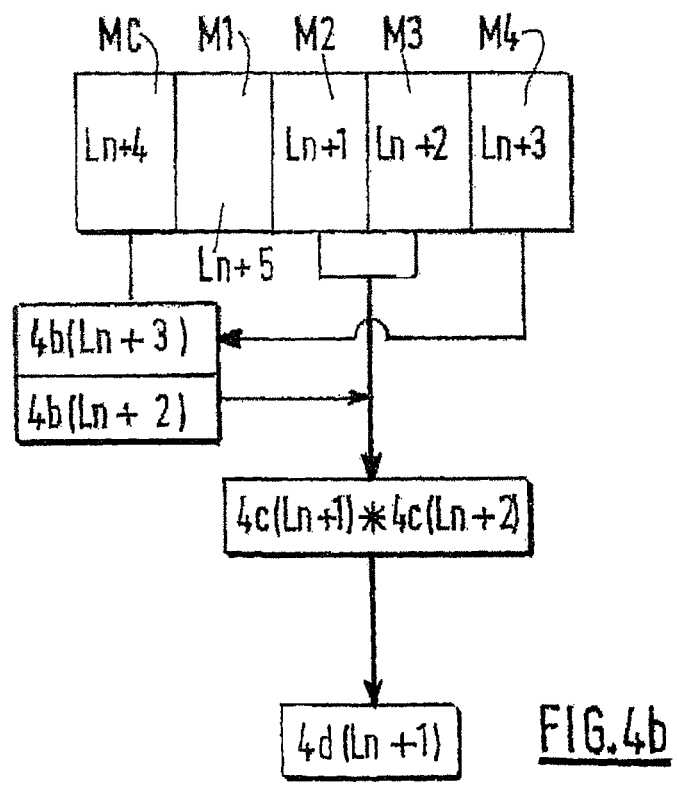

With reference to FIGS. 4a and 4b, a second implementation of an ultrasound line processing method in conformance with the invention is described.

According to this method, 5 memories M0, M1, M2, M3 and M4 are implemented to store lines of data Li relative to an acquisition comprising m lines. Thus, i varies between 1 and m.

FIG. 4a illustrates the use of memories M0, M1, M2, M3, M4 when line. L(n+4) is being formed. At this stage:

memory M0 is dedicated to the acquisition or formation of line. L(n+4).

memories. M1 and M2 are respectively dedicated to lines Ln and Ln+1. The latter are being processed to determine an intrinsic displacement 4d(Ln) by means of a corrected partial acquisition 4c(Ln) 4c(Ln+1).

memories. M3 and M4 are respectively dedicated to lines Ln+2 and Ln+3 that are being processed to determine a parameter 4b(Ln+2) relative to the displacement.

It should be noted that, at this stage of the calculation, the parameter 4b(Ln+1) relative to the displacement was calculated and stored during the previous steps from lines. Ln+1 and Ln+2.

FIG. 4b illustrates the use of these same memories. M0, M1, M2, M3 and M4 when line L(n+5) is being formed. At this stage, line. Ln is no longer necessary and may be eliminated such that:

memory M1 is dedicated to the acquisition of line L(n+5).

memories. M2 and M3 still store lines Ln+1 and Ln+2 that are henceforth used to determine an intrinsic displacement 4d(Ln+1) by using the relative displacement parameter 4b(Ln+1) that was previously calculated and stored for these two lines.

memories M4 and M0 are respectively dedicated to lines Ln+3 and Ln+4 that are henceforth used to determine a relative displacement parameter 4b(Ln+4).

At this stage of the calculation, the relative displacement parameter determined from lines Ln+2 and Ln+3 was calculated at the previous step and is stored.

In summary, memories M0, M1, M2, M3 and M4 are successively allocated to the formation of a line, to the storage of this line for calculating the parameter relative to the displacement or to the storage of this line for calculating the intrinsic displacement.

It should be noted that a device in conformance with the invention is extremely compact, which enables it to be positioned within the head of a probe, contrary to device 10 according to the prior art, which must be offset from the probe on a dedicated unit.

Independently from the position of the device, the transducer implemented to form lines may present one or more element or elements intended for transforming ultrasound waves, reflected by the biological tissues, into electrical signals.

When several, elements are used, these ultrasound lines may be formed thanks to the electronic focusing obtained by forming a channel with at least one transducer comprising several elements.

In addition, the relative displacement of the transducer in relation to the observed tissues is obtained by a calculation performed from ultrasound data in the embodiment described.

However, this relative displacement may also be determined by means of an external physical measurement, such as the position of said transducer with relation to a given referential, or by shaping a biophysical measurement, such as a signal obtained from a heart or respiratory rate.

Different variations of the invention are also possible by determining the intrinsic displacement of the tissues according to various parameters, such as at least one of the following parameters or a derivative of such a parameter: a measurement of displacement, speed, deformation speed or deformation measurement.

Similarly, the invention may be implemented by processing by parallel systems lines specific to the same acquisition in conformance with the invention. In this case, different relative displacement parameters may be simultaneously obtained in order to obtain an intrinsic displacement $3d$, as shown in FIG. 3.

The acquisition time reduction is such that it is possible to measure the VP practically at the same time as the last shot is emitted.

Such rapidity increases the ease of use of the device and allows different operating procedures to be put in place. For example, a "sequential" operating procedure, such that the device performs a limited number of acquisitions, or a "continuous" or "real time" operating procedure, such that the device continuously measures a VP value of the observed tissues, may be put in place.

Advantageously, the device comprises a visual display on which the VP of the medium is displayed. The latter may be updated as and when the acquisitions are made in numerous forms, such as, for example, by retaining the instantaneous value, by retaining the median value or the mean value from the start of the acquisitions, by retaining the median value or the mean value from a fixed duration (for example 2 seconds).

Figure 5:
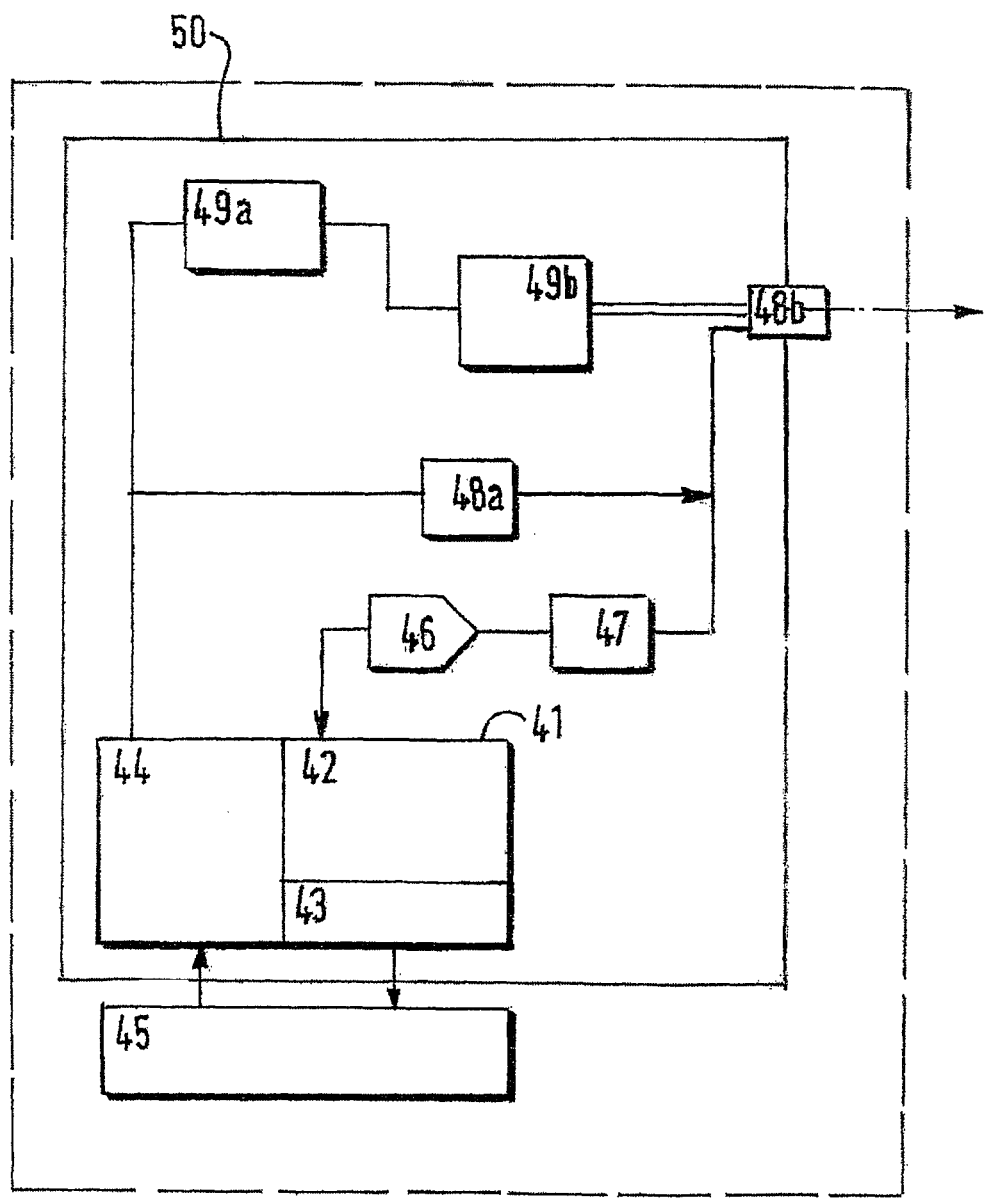
FIG. 5 is an electronic diagram of a VP measuring device according to the invention.

A diagram of a device 50 in conformance with the invention is described below by using FIG. 5.

Device 50 is composed of a linear motor 49b allowing the displacement of a mono-element ultrasound transducer 48b. Thus and as known in the prior art, the ultrasound transducer is used both as the point, for generating a low-frequency elastic wave and as a tool for visualizing this wave thanks to the ultrasound. The electronic system also includes an amplifier 49a allowing the motor 49b to have sufficient power to generate the elastic wave.

An amplifier 48a allows the transducer 48b to have sufficient power to generate the ultrasound acoustic waves.

The electronic system also comprises a preamplification and filtering system 47 and an Analog-Digital converter 46 in order to provide the ultrasound lines described in the invention to the calculator 41.

Calculator 41 consolidates the following elements in the same physical component:

An acquisition controller 44, allowing the sequences of ultrasound shots and the emission of elastic waves to be controlled A displacement calculator 42 implementing the invention described by the present patent, Optionally, an elasticity calculator 43, using data from 42 to obtain the desired elasticity measurement.

Optionally, the calculator 41 may also include the management of a user interface 45, allowing all calculation functions of the apparatus to be integrated in a very small volume.

The device thus described particularly allows all functions to be integrated near the transducer itself. This allows the transfer and intermediate storage of data to be limited as much as possible. This presents several advantages, particularly in terms of the overall compactness of the device, and the cost or quality of measured signals.

The present invention is capable of variations, particularly by performing various operations, such as the determination of the relative displacement parameter, by means of more than two lines that are successive or not successive.

In one variation, the device comprises several transducers or elements such that the ultrasound line corresponding to shot i is a matrix formed by the data received from different groups of elements according to the time.

In one variation, the device is associated with a transducer such as that described in patent application FR 0652140, filed on 15 Jun. 2006 by the Echosens company, whose content is incorporated in this application for reference.

Such a device processes several acquisitions performed concurrently over several geometrical axes.

The invention is described above by way of example. It is understood that the person skilled in the art is in a position to carry out different variations of the device and method for measuring the elasticity of a human or animal organ, particularly by combining said device and/or method with an endoscopy, laparoscopy or biopsy device and/or method or any other device or method of the type without necessarily departing from the scope of the patent.

The invention claimed is:

1. A device configured to measure the viscoelastic properties of biological tissues using a processing of ultrasound waves reflected by the biological tissues when a shear wave runs across them, the device comprising:
    memories configured to form lines of data such that each line comprises data relative to the ultrasound waves reflected from a same shot,
    a calculator configured to determine a relative parameter that is relative to a displacement between the tissues and a transducer emitting the shots,
    a calculator configured to calculate an intrinsic displacement of a medium from a set of lines forming an acquisition, and
    a calculator configured to process first ultrasound lines, by using the relative parameter, before or during the formation of second ultrasound lines from a same acquisition, in order to determine the intrinsic displacement of the biological tissues from said first lines.

2. The device according to claim 1, wherein said calculator configured to calculate the intrinsic displacement is configured to calculate the intrinsic displacement for a given time and at a given depth.

3. The device according to claim 1, wherein the device comprises a calculator configured to form, with different intrinsic displacements, a chronological table such that each column or line of the table is a function of the depth at which the intrinsic displacements are measured.

4. The device according to claim 3, wherein the calculation time of an intrinsic displacement is less than the time separating two successive ultrasound shots.

5. The device according to claim 4, wherein a memory allocated to a first ultrasound line is made available after its processing to store a second subsequent ultrasound line.

6. The device according to claim 5, wherein the device is configured to process ultrasound waves with two first memories dedicated to a calculation of intrinsic displacement, and a third memory storing a line being acquired.

7. The device according to claim 1, wherein said calculator configured to process the first ultrasound lines is configured to perform operations linked to forming an ultrasound line and to calculating intrinsic displacement.

8. The device according to claim 1, wherein the ultrasound lines come from a same emitter/receiver element.

9. The device according to claim 1, wherein the ultrasound lines are formed with an electronic focusing with at least one transducer comprising several elements.

10. The device according to claim 1, wherein the device is configured to calculate a relative displacement of a transducer with relation to the observed biological tissues by using at least:
- one external physical measurement,
- shaping of a biophysical measurement, or
- a calculation performed from ultrasound data.

11. The device according to claim 10, wherein the external physical measurement is a position of said transducer with relation to a given referential, and wherein the biophysical measurement is a signal obtained from a heart or respiratory rate.

12. The device according to claim 1, wherein the intrinsic displacement represents or derives from at least one of the following elements: a measurement of displacement, speed, deformation speed or deformation measurement.

13. The device according to claim 1, wherein the device is configured such that different acquisitions performed on different geometrical axes are concurrently processed.

14. The device according to claim 1, wherein the device is configured such that successive measurements are carried out continuously.

15. A method to measure the viscoelastic properties of biological tissues using a processing of ultrasound waves reflected by the biological tissues when a shear wave runs across them, using a device of the method comprising:
- arranging lines of data with memories such that each line comprises data relative to the ultrasound waves reflected from the same shot,
- determining a relative parameter that is relative to a displacement between the tissues and a transducer emitting shots,
- calculating an intrinsic displacement of a medium from a set of lines forming an acquisition, and
- processing two first ultrasound lines, by using the relative parameter, before or during the formation of second ultrasound lines of a same acquisition, in order to determine the intrinsic displacement of biological tissues from the first lines.

16. A probe dedicated to viscoelastic properties measurement of biological tissues by elastography, wherein the probe comprises a device in conformance with claim 1.

* * * * *